United States Patent [19]

Tau

[11] Patent Number: 5,053,562
[45] Date of Patent: Oct. 1, 1991

[54] PROCESS FOR MAKING 1,3-DIOLS FROM EPOXIDES

[75] Inventor: Kwoliang D. Tau, Corpus Christi, Tex.

[73] Assignee: Hoechst Celanese Corporation, Somerville, N.J.

[21] Appl. No.: 560,709

[22] Filed: Jul. 31, 1990

[51] Int. Cl.$^5$ .................. C07C 29/36; C07C 31/20; C07C 35/08; C07C 33/26

[52] U.S. Cl. .................. 568/867; 568/811; 568/831

[58] Field of Search .............. 568/867, 831, 811, 841

[56] References Cited

U.S. PATENT DOCUMENTS

| | | | |
|---|---|---|---|
| 3,054,813 | 9/1962 | Niederhauser | 260/398 |
| 3,463,819 | 8/1969 | Smith et al. | 260/602 |
| 3,687,981 | 8/1972 | Lawrence et al. | 260/340.7 |
| 4,873,378 | 10/1989 | Murphy et al. | 568/867 |
| 4,873,379 | 10/1989 | Murphy | 568/867 |
| 4,935,554 | 6/1990 | Murphy et al. | 568/867 |

FOREIGN PATENT DOCUMENTS

| | | | |
|---|---|---|---|
| 873073134 | 8/1987 | European Pat. Off. | 568/867 |
| 1287046 | 11/1989 | Japan | 568/841 |

OTHER PUBLICATIONS

Yokokawa et al., Bulletin of the Chemical Society of Japan, vol. 37, p. 677, 1964.
Synthetic Organic Chemicals, Eastman Kodak, vol. VII, No. 3, Rochester, NY 1934.

Primary Examiner—J. E. Evans
Assistant Examiner—Rebecca Cook
Attorney, Agent, or Firm—Donald R. Cassady

[57] ABSTRACT

A process for manufacturing 1,3-glycols is disclosed. The process comprises reacting an epoxide with synthesis gas in the presence of rhodium, a phosphine, and a lower-alkyl iodide or β-hydroxy lower-alkyl iodide.

15 Claims, 1 Drawing Sheet

Reaction conditions: 110°C, 2500 psig, 2:1 H2/CO

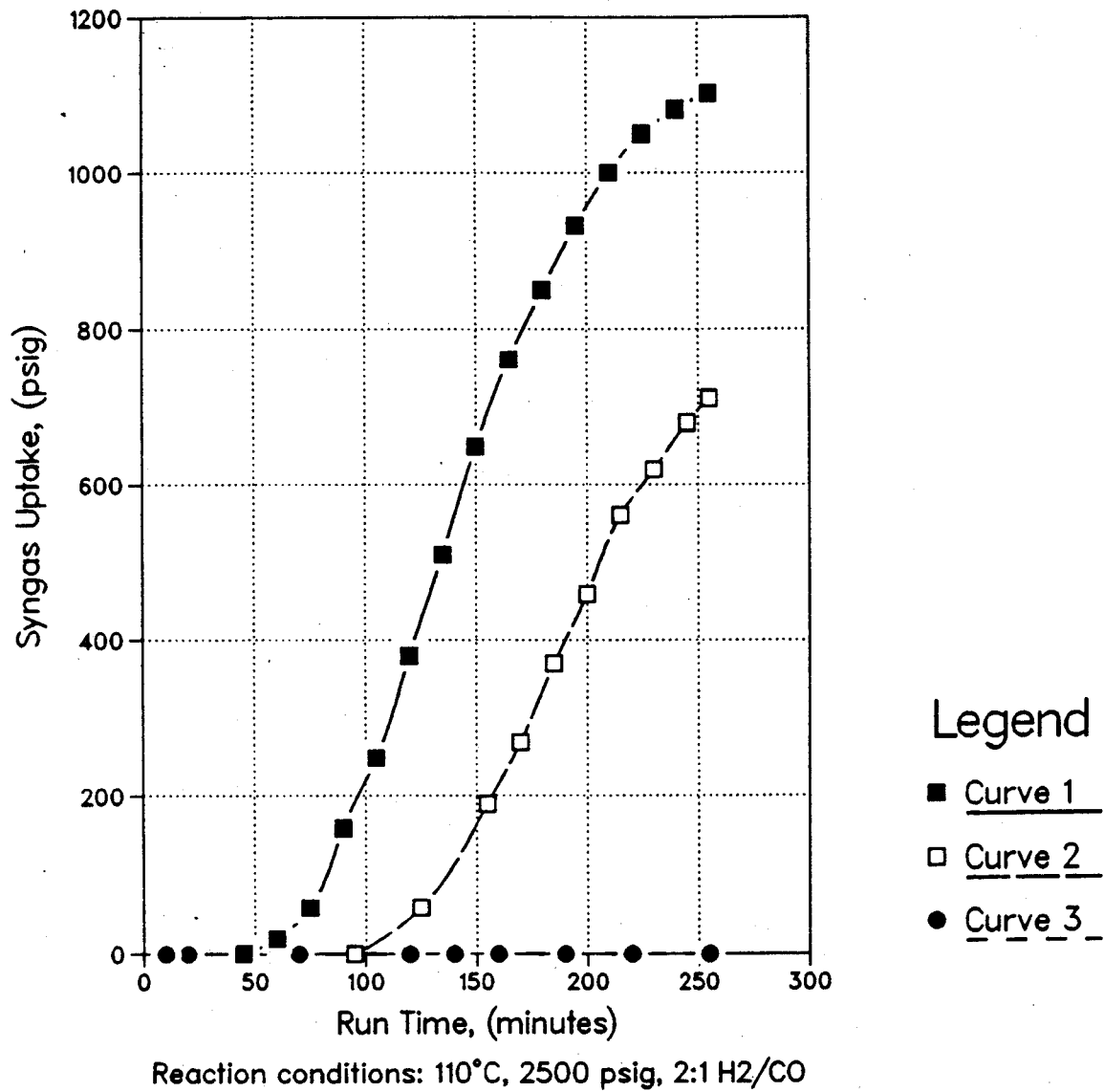

PROCESS FOR MAKING 1,3-DIOLS FROM EPOXIDES

BACKGROUND OF THE INVENTION

This invention relates to the manufacture of 1,3-diols from an epoxide. In one embodiment, this invention relates to the manufacture of 1,3-propanediol from ethylene oxide.

Glycols in general are valuable chemical compounds which find a wide variety of utilities. Such compounds are used, for example, as chemical intermediates in the manufacture of esters, as well as in the synthesis of polyesters. 1,3-Propanediol (1,3-PDO), also referred to as 1,3-propylene glycol or trimethyleneglycol, in particular, has been found to be especially useful in a number of applications. Typically, 1,3-propanediol has been prepared by acid-catalyzed hydration of acrolein to form 3-hydroxypropanal which is subsequently hydrogenated to the corresponding glycol. The high cost of acrolein and the relatively low yields obtained in such reactions have not led to commercial processes for production of 1,3-propanediol which are cost competitive with other commercially available diols which in many instances can be substituted for 1,3-propanediol.

The preparation of 1,3-glycols by the hydroformylation of epoxides, utilizing phosphine-modified cobalt carbonyl complexes as the catalyst, is shown in U.S. Pat. No. 3,463,819. In particular, said patent shows the production of 1,3-propanediol by hydroformylation of ethylene oxide, using a tertiary phosphine-modified cobalt carbonyl catalyst. Although high yields (92%) of 1,3-propanediol were claimed to have been produced in diethyl ether solvent, catalyst concentrations were extremely high, the amount of ethylene oxide charged was low, and no indication of reaction times nor reaction rates was specified. This high catalyst concentration may have been necessary because of the limited catalyst turn-over i.e.; 2-4 moles of product/mole of cobalt and phosphine. Yields of 1.3-propanediol were substantially lower in solvents other than diethyl ether.

U.S. Pat. No. 3,687,981 is also directed to a process for manufacturing 1,3-propanediol. However, the process disclosed in the '981 patent employs two separate stages. In the first stage ethylene oxide undergoes a hydroformylation reaction to produce hydroxyethyl hydroxy dioxane which is insoluble in the initial reaction solvent. The dioxane compound is separated from the initial reaction solvent and is subsequently catalytically hydrogenated to form trimethylene glycol. The patent generally discusses the possibility of using as the hydroformylation reaction catalyst, transition metals, particularly those of Group VIII of the Periodic Table, e.g., cobalt carbonyl tertiary phosphine and rhodium carbonyl. However, the examples in said patent are limited to the use of dicobalt octacarbonyl catalyst.

U.S. Pat. No. 3,054,813 is directed toward a process for the production of 3-hydroxyaldehydes or alpha-beta unsaturated aldehydes by the reaction of epoxides with synthesis gas. Said patent shows the use of a cobalt carbonyl catalyst for the hydroformylation of ethylene oxide, but the product which resulted was acrolein.

In an article by Yokokawa et al., Bulletin of the Chemical Society of Japan (Vol. 37, page 677, 1964), there is shown an attempt to hydroformylate ethylene oxide and propylene oxide using a cobalt carbonyl catalyst. In the case of ethylene oxide, the product was overwhelmingly composed of acetaldehyde. Small amounts of acrolein were formed. In the case of propylene oxide, under some conditions reasonable yields of 3-hydroxybutyraldehyde were produced, but the production of 1,3-butanediol is not mentioned.

It is likely that processes which produce 1,3-glycols from epoxides using "hydroformylation" catalysts, produce 3-hydroxyaldehydes as chemical intermediates which can either be hydrogenated to 1,3-glycols in situ, or isolated in some manner (as in the form of the aforementioned hydroxyalkyldioxanes) and then hydrogenated in a separate step. However, 3-hydroxyaldehydes, such as 3-hydroxypropanal, are unusually reactive species and readily undergo a variety of side reactions. In a literature review entitled "New Synthesis With Carbon Monoxide", B. Cornils, *Springer Verlag*, page 131, 1980, it was stated that numerous attempts had been made to subject oxiranes (epoxides) to the hydroformylation reaction to produce hydroxyaldehydes and that on account of the greater reactivity, not only of epoxides, but also of the resulting hydroxyaldehydes, the epoxide hydroformylation generally led to the formation of a mixture of products and thus unsatisfactory yields.

Under the conditions of a hydroformylation reaction, isomerization of ethylene oxide to acetaldehyde (which is sometimes further hydrogenated to ethanol) can occur. Furthermore, if hydroformylation of ethylene oxide to 3-hydroxypropanal is successful, the 3-hydroxypropanal can dehydrate to yield acrolein, which can be hydrogenated to propanal or propanol, or the 3-hydroxypropanal can undergo condensation (aldol) reactions with other aldehyde molecules to give $C_6$ branched aldehydes, which can undergo dehydration and hydrogenation reactions. It is therefore highly desirable that a catalyst for the production of 1,3-propanediol from ethylene oxide should be able to rapidly hydrogenate 3-hydroxypropanal in situ before undesirable side reactions can occur. Such a catalyst would have the economic advantage of producing the 1,3-propanediol product in a single reactor, without the need for a large and expensive apparatus for the isolation and subsequent hydrogenation of aldehydes.

Thus, until recently, there remained a need for an effective method for manufacturing 1,3-glycols, especially from epoxides, which process is usable in a commercial manner. Recently, two patents, U.S. Pat. Nos. 4,873,378 and 4,873,379 have disclosed a one-step method for the manufacture of 1,3-diols from epoxides using a rhodium catalyst. U.S. Pat. No. 4,873,378 claimed a rhodium/phosphine catalyzed hydrocarbonylation procedure in the presence of a strong acid, as for example HI, HCl, methanesulfonic acid, and the like. In U.S. Pat. No. 4,873,379, a rhodium-catalyzed hydrocarbonylation procedure in the presence of an alkali metal ion, as for example from a salt of an alkali metal ion was claimed.

SUMMARY OF THE INVENTION

It has now been discovered that the reaction rate for the conversion of epoxides into 1,3-glycols by a rhodium-phosphine catalyzed hydrocarbonylation reaction is significantly increased in the presence of a lower-alkyl iodide or a $\beta$-hydroxy lower-alkyl iodide.

Thus, the present invention provides a process for manufacturing 1,3-glycols of the formula

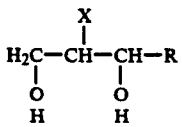

wherein R represents hydrogen, a monovalent aliphatic or aromatic group having from one to about twelve carbon atoms, or a divalent aliphatic group having from 4 to about 6 carbon atoms which together with X forms a cyclic structure, and X represents hydrogen, or if R is divalent, a bond with R. The process comprises reacting an epoxide of the formula

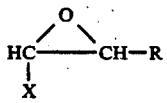

wherein R and X have the aforementioned meaning, with CO and $H_2$ in a suitable reaction solvent, wherein said process is characterized in that the reaction mixture contains (1) an epoxide of the foregoing structure at a concentration of from about 0.01 to about 30 weight %; (2) rhodium at a molar concentration from about 0.00001 to about 0.1 molar; (3) a phosphine having the formula

$PR_1R_2R_3$ wherein $R_1$, $R_2$, and $R_3$ are independently selected from the group consisting of aliphatic, cyclo-aliphatic, and aromatic hydrocarbon groups, the molar ratio of rhodium to phosphine being from about 10:1 to about 1:10; (4) CO; (5) $H_2$; wherein the molar ratio of CO to $H_2$ is from about 10:1 to about 1:10; and (6) a lower-alkyl iodide or β-hydroxy lower-alkyl iodide at a molar concentration of from about 0.00001 to about: 0.1 molar; wherein the reaction takes place at a temperature from about 50 to about 200° C. under a pressure from about 200 to about 10,000 psig, for a period of time which is sufficient to form at least some of the desired 1,3-glycol.

DETAILED DESCRIPTION OF THE PREFERRED EMBODIMENTS

As indicated above, the process of the present invention provides a method for the manufacture of 1,3-glycols through the hydrocarbonylation of epoxides. The desired glycols therefore contain one more carbon atom and one more oxygen atom than the epoxide. Thus, for example, when the epoxide reactant is ethylene oxide, containing 2 carbon atoms, the resultant 1,3-glycol is 1,3-propanediol, containing 3 carbon atoms. Examples of other specific epoxides which are useful in the present invention include propylene oxide, 1,2-epoxyoctane, cyclohexene oxide, and styrene oxide.

The epoxides, as indicated previously, have the general formula

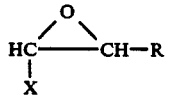

wherein R is hydrogen, a monovalent aliphatic or aromatic group having from one to about twelve carbon atoms, or a divalent aliphatic group having from 4 to about 6 carbon atoms which together with X forms a cyclic structure, and X represents hydrogen or, if R is divalent, a bond with R. R therefore may be a monovalent alkyl group containing, for example, from one to six carbon atoms or may be a divalent alkyl group or an aromatic group, such as a phenyl group. If, for example, R is a divalent alkyl group having four carbon atoms, then the epoxide is cyclohexene oxide. The epoxide is usually present in the reaction mixture at a concentration of from about 0.01 to about 30 weight percent. Typically the concentration of epoxide is from about 0.5 to 20 weight percent.

The various epoxides may require different reaction conditions, to achieve optimum results in terms of product yield and selectivity, as well as different specific rhodium, phosphine, or acid components. Using the system comprising rhodium and tricyclohexylphosphine, ethylene oxide gives good product yield and selectivity. Conditions for other epoxides may possibly be optimized to achieve better product yield and selectivity.

The carbonylation reaction, as indicated previously, takes place in a suitable solvent. As a general principle, solvents which may be categorized as having medium to high polarity are suitable, such as aromatic solvents, ethers, polyethers, amides, sulfones, and alcohols. Depending upon the reactivity of the particular solvent selected and the specific conditions to be employed, ketones, and esters may also be usable. The preferred solvents generally are high molecular weight: ethers, polyethers, and cyclic ethers, especially glycol polyethers. An especially preferred solvent is tetraglyme, the dimethylether of tetraethylene glycol, 2,5,8,11,14-pentaoxapentadecane. Particularly useful solvents also include tetrahydrofuran, diglyme, and Ucon TM oils which are mixed glycol polyethers of ethylene and propylene glycol subunits.

To be suitable, a solvent should solubilize the epoxide reactant. Preferred solvents should not substantially react with any of the components of the reaction mixture or the desired product. Thus, for lower molecular weight epoxides and glycols, solvents such as tetraglyme, tetrahydrofuran and the like are usually used. For higher molecular weight epoxides and glycols, hydrocarbon solvents such as petroleum ethers, toluene, and xylene may be appropriate. The latter solvents are less suitable for lower molecular weight epoxides and glycols such as ethylene oxide and 1,3-propanediol.

The lower-alkyl iodide can be selected from the group consisting of methyl iodide, ethyl iodide, n-propyl iodide, isopropyl iodide, n-butyl iodide, isobutyl iodide, sec.-butyl iodide, and tert.-butyl iodide. The β-hydroxy lower-alkyl iodide can be a member of the group consisting of 2-hydroxyethyl iodide, 1-(2-iodo)-propanol, 2-methyl-2-iodo-1-propanol, 2-methyl-1-iodo-2-propanol, 2-(1-iodo)propanol and the like.

The concentration of the lower-alkyl iodide or β-hydroxy lower-alkyl iodide in the reaction solvent should be in the range from about 0.00001 molar to about 0.1 molar. Preferably, the concentration of lower-alkyl iodide or β-hydroxy lower-alkyl iodide will be from about 0.005 to about 0.1 molar.

The rhodium which is employed in the present process may be introduced in the form of rhodium metal, rhodium salts, and/or rhodium complexes. The only proviso is that the rhodium complex should not contain ligands which insolubilize or poison the catalyst. Thus, selection of the particular rhodium component may, in part, depend upon the solubility of the particular rhodium metal or compound in the specific solvent utilized as the reaction medium. The rhodium useful in the practice of the present invention includes rhodium metal, rhodium oxides, $RhI_3$, $RhBr_3$, $RhCl_3$, $Rh(Acac)_3$, $Rh(CO)_2Acac$, $Rh_6(CO)_{16}$, $[RhCl(CO)_2]_2$ and $Rh(NO_3)_3$, wherein Acac represents acetylacetonate. Likewise, the rhodium useful in the practice of the present invention may be a rhodium carbonyl-phosphine complex which has been preformed prior to introduction into the reaction mixture, using any suitable technique for preforming such complexes.

The concentration of the rhodium in the reaction solvent should be in the range from about 0.00001 molar to about 0.1 molar. Preferably, the concentration of rhodium will be from about 0.005 to about 0.1 molar.

The phosphine which is employed in the present invention has the general formula $$PR_1R_2R_3$$

wherein $R_1$, $R_2$, and $R_3$ are all independently selected from the group consisting of aliphatic, cyclo-aliphatic, and aromatic radicals. Preferably, $R_1$, $R_2$, and $R_3$ are all alkyl groups containing from about 1 to about 12 carbon atoms. Particularly preferred alkyl groups include methyl, ethyl, n-propyl, isopropyl, n-butyl, iso-butyl, sec-butyl, and cyclohexyl. Aryl and mixed aryl/alkyl phosphines may be used in the present invention, but their efficacy is dependent upon the particular reaction conditions, including solvent, which are employed. In general, the aryl and mixed aryl/alkyl phosphines are not as efficacious as the trialkylphosphines. The most preferred phosphine is tricyclohexylphosphine. Tri-isopropylphosphine and tri-isobutylphosphine have also been found to be extremely useful.

The amount of phosphine employed is not critical, but in general, it has been found that a molar ratio of rhodium to phosphine of about 1:1 is preferred. Broadly, a range of about 10:1 to about 1:10 is operable, however. Typically, the molar ratio of rhodium to phosphine will be from about 4:1 to about 1:4.

The ratio of hydrogen to carbon monoxide employed in the hydrocarbonylation reaction should be equal to or greater than 1:2 and preferably no greater than about 5:1, although acceptable yields are realized at concentrations in narrow ranges on both sides of the preferred range.

With respect to the pressure employed during the hydrocarbonylation reaction, the pressure is not critical and generally falls within the range from about 200 to about 10,000 psig. Preferably, the pressure falls in the range of from about 1,000 to about 4,000 psig.

The temperature used in the carbonylation reaction also is not critical. As a general proposition, it has been found that increasing temperature also increases rates. However, increasing temperatures may have an adverse affect on selectivity. Thus, some balancing of temperature is required in order to achieve suitable rates and suitable selectivities. Generally, a temperature of from about 50° to about 200° C. will be employed, preferably from about 100° to about 150° C.

As a general proposition, with respect to $H_2$:CO composition, reaction pressure, and reaction temperature, all will vary somewhat based upon the particular reaction conditions employed and adjustment thereof is within the ordinary skill of one in the art.

The present invention is further shown by the following non-limiting examples.

GENERAL EXPERIMENTAL METHOD EMPLOYED IN THE EXAMPLES

All examples were performed in a batch autoclave unit which consisted of a 300 cc Hastelloy autoclave, equipped with remotely operable controls for feeds, vents, stirring, heating, cooling, and the like. High-pressure type fittings, valves, and tubings were employed.

All catalysts and solvents were weighed under nitrogen and rapidly charged to a cold autoclave which was then purged twice with nitrogen and twice with synthesis gas. Subsequently, the autoclave was pressurized with synthesis gas to the desired pressure and heated under slow stirring to reaction temperature, over a period of 0.5 to 4.0 hours. Ethylene oxide was then injected into the autoclave from either a pressurized blowcase bomb or a Ruska syringe pump, at which time fast stirring was commenced and the total reactor pressure raised to the final desired value, using synthesis gas to control the pressure. Constant reactor pressures were maintained automatically during the runs by feeding synthesis gas on demand from a high-pressure synthesis gas reservoir of known volume. The uptake of reaction synthesis gas was monitored by periodic measurement of the pressure of the synthesis gas reservoir. Runs were terminated, usually when synthesis gas uptake slowed to nearly zero, by slowing the stirring rate, terminating the synthesis gas feed, and cooling the reactor as rapidly as possible, typically over a 30 to 60 minute period.

Small quantities of ethylene oxide were injected into the reactor which was hot and pressurized, using either a Ruska syringe or a pressurized blowcase bomb by condensation of ethylene oxide vapor under pressure from a lecture bottle, into the blowcase bomb. When ethylene oxide had been charged to the blowcase bomb, the blowcase bomb was detached from the transfer apparatus, weighed, then connected to the autoclave.

When the Ruska pump method was used for injecting the ethylene oxide, liquid ethylene oxide was transferred through stainless steel lines to the Ruska syringe pump which then injected the ethylene oxide into the autoclave unit.

Because liquid ethylene oxide became held up in the lines, fittings, and valves leading to the autoclave, it was necessary to charge somewhat larger than theoretical quantities of ethylene oxide to the Ruska pump and then calibrate the unit for the quantity of ethylene oxide which actually reached the autoclave. Calibration runs were performed by charging the reactor with 100 grams of water and 1.8 grams of sulfuric acid and heating it to 100° C. Ethylene oxide was then charged to the Ruska pump, injected into the reactor, which was then heated for two hours to achieve ethylene oxide hydrolysis to ethylene glycol. The resulting ethylene glycol:water solutions were analyze for ethylene glycol using gas chromatography. In a typical run, 12.0 grams of ethylene oxide would be charged to the Ruska pump and the ethylene glycol equivalent of 10.0 grams of ethylene oxide reached the reactor. Ethylene oxide feed was then back-calculated from the ethylene glycol and plots of ethylene oxide observed versus ethylene oxide charged, were constructed. Such plots were found to be reasonably linear over the range of 5 to 15 grams of ethylene oxide and typically showed 75 to 85 percent ethylene oxide efficiency in the transfer operation. The results of such calibration runs were then used to calculate ethylene oxide feed for the catalytic carbonylation runs.

With respect to the materials employed in the Examples, [RhCl (CO)$_2$]$_2$, P(C$_6$H$_{11}$)$_3$ and P(n—C$_4$H$_9$)$_3$ were purchased from Strem Chemicals and stored and handled under nitrogen. Rh(CO)$_2$Acac was either purchased from Englehard or prepared from RhCl$_3$.3H$_2$O, acetylacetone, and dimethylformamide and then recrystallized from hexane to yield green-red crystalline needles.

Ethylene oxide (99.7% min) was purchased from MG Industries and stored in chilled water. H$_2$/CO mixtures were purchased from Iweco and Big Three. Tetraglyme was received was received from Aldrich and then distilled from calcium hydride under nitrogen.

In the following examples where yields are quoted, yields were calculated from the observed moles of product divided by the moles of EO calculated to have been charged to the reactor.

EXAMPLE 1

Eighty grams of tetraglyme, 1.06 g water, 0.52 g of Rh(CO)$_2$Acac, 0.28 g of methyl iodide, and 0.56 g of tricyclohexylphosphine were charged into a 300 cc autoclave according to the standard procedure. The mixture was heated to 110° C. under a pressure of 2120 psig of 2:1 H$_2$/CO. The pressure was increased to 2500 psig with the addition of 12.5 g ethylene oxide. Uptake of the gas began after an induction period of about 45 minutes. The gas uptake in psig was recorded at regular intervals. The reaction was terminated after 4 hours 15 minutes and the product removed and analyzed according to the standard procedure. The product contained 66.14% yield of 1,3-PDO and minor amounts of several by-products.

EXAMPLE 2

Following the procedure of Example 1, 80 g tetraglyme, 1.07 g water, 0.52 g Rh(CO)$_2$Acac, 0.35 g 2-iodoethanol, and 0.55 g tricyclohexylphosphine were contacted with 2:1 H$_2$/CO and 12.3 g ethylene oxide. After an induction period of 1¼ hours the reaction proceeded to substantial completion within 4½ hours yielding 68.91% 1,3-PDO.

COMPARISON EXAMPLE 1

Following the procedure of Example 1, 80 g tetraglyme, 1.07 g water, 0.52 g Rh(CO)$_2$Acac, and 0.33 g methyl iodide were contacted with 2:1 H$_2$/CO and 12.5 g ethylene oxide. No uptake of syngas occurred over a 4½ hour reaction time.

COMPARISON EXAMPLE 2

Following the procedure of Example 1, 80 g tetraglyme, 1.07 g water, 0.52 g Rh(CO)$_2$Acac, and 0.56 g tricyclohexylphosphine were contacted with 2:1 H$_2$/CO and 12.5 g ethylene oxide. After an induction period of 1 7/12 hours the reaction proceeded slowly. After 4½ hours the reaction was terminated and the products determined. Total yield of 1,3-PDO was 37.2%.

A comparison of syngas uptake over the 4½ hour reaction time of Example 1, and Comparative Examples 1, and 2 is presented in the drawing. Curve 1 represents the syngas uptake over time for Example 1. Curve 2 represents the syngas uptake over time for Comparative Example 2. Curve 3 represents the syngas uptake over time for Comparative Example 1.

What is claimed is:

1. A single step process for manufacturing 1,3-glycols of the formula

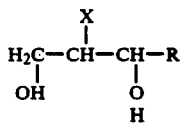

wherein R represents hydrogen, a monovalent aliphatic or aromatic group having from one to about twelve carbon atoms, or a divalent aliphatic group having from 4 to about 6 carbon atoms which together with X forms a cyclic structure, and X represents hydrogen, or if R is divalent, a bond with R, wherein said process comprises reacting an epoxide of the formula

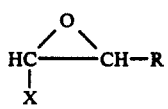

wherein R and X have the aforementioned meaning, with CO and H$_2$ in a suitable reaction solvent, said process being characterized in that the reaction mixture comprises (1) an epoxide of the foregoing structure at a concentration from about 0.01 to about 30 weight percent; (2) rhodium at a molar concentration from about 0.00001 to about 0.1 molar; (3) a phosphine having the formula

wherein R$_1$, R$_2$, and R$_3$ are independently selected from the group consisting of aliphatic, cyclo-aliphatic, and aromatic hydrocarbon groups, the molar ratio of rhodium to phosphine being from about 10:1 to about 1:10; (4) CO; and (5) H$_2$; wherein the molar ratio of CO to H$_2$ is from about 10:1 to about 1:10; and (6) a member of the group consisting of lower-alkyl and β-hydroxy lower-alkyl iodides at a molar concentration of from about 0.00001 to about 0.1 molar; and wherein the reaction takes place at a temperature from about 50° to about 200° C. under a pressure from about 200 to about 10,000 psig, for a period of time which is sufficient to form at least some of the desired 1,3-glycol.

2. The process of claim 1 wherein the epoxide is selected from the group consisting of ethylene oxide, propylene oxide, octene oxide, and cyclohexene oxide.

3. The process of claim 1 wherein the solvent is an ether or a mixture thereof.

4. The process of claim 3 wherein the solvent is selected from the group consisting of tetraglyme, tetrahydrofuran, and a mixture of glycol polyethers of ethylene and propylene glycols.

5. The process of claim 1 wherein the rhodium is selected from the group consisting of rhodium metal, rhodium oxides, RhI$_3$, RhBr$_3$, RhCl$_3$, Rh(Acac)$_3$, Rh(CO)$_2$Acac, Rh$_6$(CO)$_{16}$, [RhCl(CO)$_2$]$_2$, and Rh(NO$_3$)$_3$.

6. The process of claim 5 wherein the rhodium is present at a concentration from about 0.005 to about 0.10 molar.

7. The process of claim 1 wherein the phosphine is a trialkyl phosphine.

8. The process of claim 7 wherein the phosphine is selected from the group consisting of tricyclohexylphosphine, triisopropyl phosphine, tri-sec-butylphosphine, tri-isobutylphosphine, tri-n-butylphosphine, and tri-n-propyl phosphine.

9. The process of claim 8 wherein the phosphine is tricyclohexylphosphine.

10. The process of claim 1 wherein the molar ratio of rhodium to phosphine is from about 1:2 to about 2:1.

11. The process of claim 1 wherein the ratio of $H_2$:CO is from about 5:1 to about 1:2.

12. The process of claim 1 wherein the pressure is from about 1000 to about 3000 psig and the temperature is from about 100° to 130° C.

13. The process of claim 1 wherein the lower-alkyl iodide is methyl iodide.

14. The process of claim 1 wherein the β-hydroxy lower-alkyl iodide is 2-iodoethanol.

15. The process of claim 1 wherein the 1,3-glycol is 1,3-propanediol, the epoxide is ethylene oxide, the solvent is tetraglyme, the reaction temperature is from about 100° to about 130° C., and the reaction pressure is from about 1000 to about 3000 psig.

* * * * *